(12) United States Patent
Chen et al.

(10) Patent No.: US 8,198,501 B2
(45) Date of Patent: Jun. 12, 2012

(54) ZEOLITE CATALYST FOR HYDROISOMERIZATION OF LIGHT PARAFFINS TO PRODUCE HIGH OCTANE GASOLINE

(75) Inventors: Cong-Yan Chen, Kensington, CA (US); Stacey I. Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/956,951

(22) Filed: Nov. 30, 2010

(65) Prior Publication Data

US 2011/0130610 A1 Jun. 2, 2011

Related U.S. Application Data

(60) Provisional application No. 61/265,310, filed on Nov. 30, 2009.

(51) Int. Cl.
*C07C 5/27* (2006.01)
(52) U.S. Cl. ....................................................... 585/739
(58) Field of Classification Search ................... 585/739
See application file for complete search history.

(56) References Cited

U.S. PATENT DOCUMENTS

| 4,910,006 A | 3/1990 | Zones et al. |
| 4,963,337 A | 10/1990 | Zones |
| 5,007,997 A | 4/1991 | Zones et al. |
| 5,082,988 A | 1/1992 | Holtermann |
| 5,120,425 A | 6/1992 | Zones et al. |
| 5,166,112 A | 11/1992 | Holtermann |
| 5,233,121 A | 8/1993 | Modica |
| 6,140,547 A | 10/2000 | Lin et al. |
| 7,029,572 B2 | 4/2006 | Maesen et al. |

OTHER PUBLICATIONS

Abstract: Hydroisomerization of Light Alkanes over Zeolites, 21$^{st}$ NAM Conference, Jun. 7-12, 2009, abstract submitted Dec. 1, 2008.

*Primary Examiner* — Thuan Dinh Dang
(74) *Attorney, Agent, or Firm* — Michael D. Ross; E. Joseph Gess

(57) ABSTRACT

The present invention is directed to a process for isomerizing light paraffins by using a catalyst containing a zeolite selected from the group consisting of CON- and TUN-type zeolites, and at least one Group VIII metal. It has been found that the CON- and TUN-type zeolite catalysts of the present invention selectively convert $C_6$ paraffins into the more favorable higher octane $C_6$ isomer, namely 2,3-dimethylbetane (RON 101.0), over the less favorable $C_6$ isomer, namely octane 2,2-dimethylbutane (RON 91.8).

19 Claims, No Drawings

ZEOLITE CATALYST FOR HYDROISOMERIZATION OF LIGHT PARAFFINS TO PRODUCE HIGH OCTANE GASOLINE

FIELD OF THE INVENTION

The present invention is directed to a process for isomerizing light paraffins by using a catalyst containing a zeolite selected from the group consisting of CON- and TUN-type zeolites, and at least one Group VIII metal.

It has been found that the CON- and TUN-type zeolite catalysts of the present invention selectively isomerize $C_6$ paraffins into the more favorable higher octane $C_6$ isomer, namely 2,3-dimethylbetane (RON 101.0), over the less favorable $C_6$ isomer, namely octane 2,2-dimethylbutane (RON 91.8).

BACKGROUND OF THE INVENTION

Modern automobile engines require high octane gasoline for efficient operation. Previously lead (Pb) and oxygenates, such as methyl-t-butyl ether (MTBE) were added to gasoline to increase the octane number. Furthermore, several high octane components normally present in gasoline, such as benzene, aromatics, and olefins, must now be reduced. Obviously, a process for increasing the octane of gasoline without the addition of toxic or environmentally adverse substances would be highly desirable.

For a given carbon number of a light naphtha component, the shortest, most branched isomer tends to have the highest octane number. For example, the branched isomers of hexane, monomethylpentane and dimethylbutane, have octane numbers that are significantly higher than that of n-hexane, with dimethylbutane having the highest research octane number (RON). Likewise, the branched isomer of pentane, methylbutane, has a significantly higher RON than n-pentane. By increasing the proportion of these high octane isomers in the gasoline pool, satisfactory octane numbers may be achieved for gasoline without additional additives.

Two types of octane numbers are currently being used, the motor octane number (MON) determined using ASTM D2700 and the RON determined using ASTM D2699. The two methods both employ the standard Cooperative Fuel Research (CFR) knock-test engine. Sometimes the MON and RON are averaged, (MON+RON)/2, to obtain an octane number. Therefore, when referring to an octane number, it is essential to know which one is being discussed. In this disclosure, unless clearly stated otherwise, octane number will refer to the RON. For comparative purposes, the RON for isomers of hexane and pentane are listed in Table 1.

TABLE 1

Research octane number (RON) values for $C_5$ and $C_6$ alkane isomers

| | |
|---|---|
| n-pentane | 61.7 |
| methylbutane | 92.3 |
| n-hexane | 24.8 |
| 2-methylpentane | 73.4 |
| 3-methylpentane | 74.5 |
| 2,2-dimethylbutane | 91.8 |
| 2,3-dimethylbutane | 101.0 |

Gasoline is generally prepared from a number of blend streams, including light naphthas, full range naphthas, heavier naphtha fractions, and heavy gasoline fractions. The gasoline pool typically includes butanes, light straight run, isomerate, FCC cracked products, hydrocracked naphtha, coker gasoline, alkylate, reformate, added ethers, etc. Of these, gasoline blend stocks from the FCC, the reformer and the alkylation unit account for a major portion of the gasoline pool. FCC gasoline, and if present, coker naphtha and pyrolysis gasoline, generally contribute a substantial portion of the pool sulfur.

Gasoline suitable for use as fuel in an automobile engine should have a RON of at least 80, preferably at least 85, and most preferably 90 or above. High performance engines may require a fuel having a RON of about 100. Most gasoline blending streams will have a RON ranging from about 55 to about 95, with the majority falling between about 80 and 90. Obviously, it is desirable to maximize the amount of dimethylbutane in the gasoline pool in order to increase the overall RON. The present invention is directed to this objective.

Hydroisomerization is an important refining process whereby the RON of a refinery's gasoline pool may be increased by converting straight chain normal or singly branched light paraffins into their more branched isomers. The hydroisomerization reaction is controlled by the thermodynamic equilibrium. At higher reaction temperatures the equilibrium shifts towards the lower octane isomers (e.g., from dimethylbutanes via methylpentanes to n-hexane). Since the high octane components (e.g., 2,3-dimethylbutane with a RON of 101.0) are the target products in this process, it is desirable to develop a more active catalyst to perform this reaction at a lower temperature.

In conventional hydroisomerization processes, light normal paraffins are isomerized to their more branched counterparts over a bifunctional catalyst having both acidity (e.g., mordenite or chlorinated amorphous alumina) and hydrogenation/dehydrogenation functionality. Several prior art catalysts have been disclosed to hydroisomerize these lower octane paraffins into the more branched, higher octane isomers (see, for example, U.S. Pat. Nos. 7,029,572 to Maesen et al. and 6,140,547 to Lin et al.).

U.S. Pat. Nos. 5,082,988 and 5,166,112 both to Holtermann each disclose a process and a catalyst for isomerizing normal and slightly branched $C_4$ to $C_7$ hydrocarbons, the catalyst comprising a Group VIII metal on Beta zeolite. Chica et al. (*J. Catalysis* 187, 167-176 (1999)) compared the hydroisomerization of light paraffins by nanocrystalline Beta zeolite and various other materials including zeolite SSZ-33. U.S. Pat. Nos. 4,910,006 and 5,007,997 both to Zones et al. disclose the isomerization of $C_4$ to $C_7$ hydrocarbons using zeolite SSZ-26, including the isomerization of pure hexane to give a product with a 2,3-dimethylbutane:2,2-dimethylbutane ratio of about 0.55. U.S. Pat. Nos. 4,963,337 and 5,120,425 both to Zones et al. disclose the isomerization of $C_4$ to $C_7$ hydrocarbons using zeolite SSZ-33. U.S. Pat. No. 5,233,121 to Modica discloses a process for isomerizing a light paraffinic naphtha feedstock using a catalyst comprising a zeolite Beta component.

There is a need for new and improved hydrocarbon hydroisomerization catalysts and processes that provide high selectivity for producing high octane isomers of light paraffins, wherein the catalysts are also highly active, environmentally benign, and readily regenerable.

SUMMARY OF THE INVENTION

According to one aspect of the present invention, there is provided a zeolite catalyst for increasing the octane number of a light paraffin stream. According to another aspect of the present invention, there is provided a process for hydroisomerizing a light paraffin feed stream to preferentially provide higher octane isomers. Processes of the present invention may comprise contacting the zeolite catalyst with a hydrocarbonaceous feed comprising relatively low octane light paraffins, such as n-hexane, under hydroisomerization conditions. In an embodiment, a CON-type zeolite is used in the catalyst. Exemplary CON-type zeolites include the aluminosilicate form of SSZ-26, SSZ-33, or CIT-1. In another embodiment, a TUN-type zeolite is used in the catalyst. Exemplary TUN-type zeolites include the aluminosilicate form of TNU-9. The CON- or TUN-type zeolite may be combined with a suitable amount of a Group VIII metal, such as platinum or palladium. The feed may comprise normal and singly branched light paraffins, e.g., $C_4$-$C_7$ paraffins, having relatively low octane numbers. In an embodiment, the feed may comprise predominantly $C_5$-$C_6$ normal paraffins.

According to another aspect of the present invention, there is provided a process for isomerizing light paraffins comprising contacting a hydrocarbonaceous feed stream with a zeolite catalyst in a hydroisomerization zone under hydroisomerization conditions in the presence of hydrogen to provide a product stream comprising at least about 10 mol % of 2,3-dimethylbutane.

According to a further aspect, the present invention provides an isomerization process comprising contacting a feed stream comprising light paraffins with a zeolite catalyst in a hydroisomerization zone under hydroisomerization conditions in the presence of hydrogen to provide a product stream having a 2,3-dimethylbutane/2,2-dimethylbutane mole ratio of at least about 1.

In still another aspect of the present invention, there is provided a process for isomerizing light paraffins comprising contacting a feed stream comprising at least about 10 vol % n-hexane with a zeolite catalyst in a hydroisomerization zone under hydroisomerization conditions in the presence of hydrogen; wherein the n-hexane is selectively isomerized to 2,3-dimethylbutane to provide a product stream having a 2,3-dimethylbutane/2,2-dimethylbutane mole ratio greater than about 1.

DETAILED DESCRIPTION OF THE INVENTION

Introduction

The term "active source" means a reagent or precursor material capable of supplying an element in a form that can react and be incorporated into the zeolite structure. The terms "source" and "active source" may be used interchangeably herein.

The term "zeolite" may include (a) intermediate and (b) final or target zeolites produced by (1) direct synthesis or (2) post-crystallization treatment (secondary synthesis). Secondary synthesis techniques allow for the synthesis of a target zeolite from an intermediate zeolite using techniques such as heteroatom lattice substitution techniques and acid leaching. For example, an aluminosilicate can be synthesized from an intermediate borosilicate by post-crystallization heteroatom lattice substitution of the Al for B. Such techniques are known, for example, as described in U.S. Pat. No. 6,790,433 to Chen et al.

Where permitted, all publications, patents and patent applications cited in this application are incorporated by reference herein in their entirety, to the extent such disclosure is not inconsistent with the present invention.

Unless otherwise specified, the recitation of a genus of elements, materials or other components, from which an individual component or mixture of components can be selected, is intended to include all possible sub-generic combinations of the listed components and mixtures thereof. Also, "include" and its variants, are intended to be non-limiting, such that recitation of items in a list is not to the exclusion of other like items that may also be useful in the materials, compositions and methods of this invention.

When used herein, the Periodic Table of the Elements refers to the version published by the CRC Press in the "CRC Handbook of Chemistry and Physics," 75th Edition (1994-1995). The names for families of the elements in the Periodic Table are given here in the Chemical Abstracts Service (CAS) notation.

In one aspect, the present invention is directed to processes for isomerizing a light paraffin feed stream, which may comprise predominantly $C_5$ and $C_6$ paraffins. Such processes may comprise contacting the light paraffin feed stream with a zeolite catalyst in a hydroisomerization zone under hydroisomerization conditions, wherein the isomer dimethylbutane is preferentially formed as compared to monomethylpentane and n-hexane In another aspect, the present invention relates to processes using a CON-type zeolite catalyst for the hydroisomerization of light paraffins to produce higher octane gasoline fuels. A refinery stream referred to as light paraffins typically contains mainly $C_4$ to $C_7$ hydrocarbons and has a relatively low octane number because it contains substantial amounts of normal $C_5$ and $C_6$ paraffins. For example, n-pentane and n-hexane have a research octane number (RON) of 61.7 and 24.8, respectively. However, when these paraffins are isomerized to form branched paraffins, their RON increases dramatically. For example, methylbutane (i.e., iso-pentane) has a RON of 92.3 while 2-methylpentane and 3-methylpentane have a RON of 73.4 and 74.5, respectively. Generally, the RON will increase with increased branching. For example, 2,2-dimethylbutane and 2,3-dimethylbutane have a RON of 91.8 and 101.0, respectively (Table 1).

In this disclosure, the isomers 2-methylpentane and 3-methylpentane may be collectively referred to as monomethylpentane. Similarly, the isomers 2,2-dimethylbutane and 2,3-dimethylbutane may be collectively referred to herein as dimethylbutane, that is to say the term "dimethylbutane" may be used herein generically and/or collectively to include both of the isomers 2,2-dimethylbutane and 2,3-dimethylbutane.

The isomers of $C_5$ and $C_6$ paraffin are included in the light naphtha fraction of the gasoline pool. One skilled in the art will recognize that some isomers of $C_7$ paraffin may also be present in the light naphtha fraction. However, heptane and its isomers are generally only present in minor amounts.

In this disclosure the terms CON-type zeolite, CON-type molecular sieve, or variations thereof refers to the framework structure code for a family of molecular sieve materials comprising zeolites SSZ-26, SSZ-33 and CIT-1. Similarly, herein the term TUN-type zeolite refers to the framework structure code for zeolite TNU-9. The Structure Commission of the International Zeolite Association (IZA) gives codes consisting of three alphabetical letters to zeolites (molecular sieves) having a structure that has been determined. Zeolites having the same topology are generically called by such three letters.

Code CON is assigned to zeolite CIT-1 which contains a three-dimensional channel system. Its first channel system has a 12-ring pore opening (6.4×7.0 Å) along [001]. Its second channel system has a 12-ring pore opening (5.9×7.0 Å) along [100]. Its third channel system has a 10-ring pore opening (4.5×5.1 Å) along [010]. Therefore, CIT is called a 12-/12-/10-ring zeolite. Details of its structure are described by Lobo and Davis in *J. American Chemical Society*, Vol. 117 (1995) pp. 3764-3779, which is incorporated herein by reference.

Both zeolites SSZ-26 and SSZ-33 are intergrowths of two similar but distinct crystalline polymorphs, according to Lobo et al. as they described the details of the structures of zeolites CIT-1, SSZ-26 and SSZ-33 in the journal *Science*, Vol. 262 (1993) pp. 1543-1546, which is incorporated herein by reference. Each polymorph of SSZ-26 and SSZ-33 is a 12-/12-/10-ring zeolite structure. One of these two polymorph structures is CIT-1. Therefore, SSZ-26, SSZ-33, and CIT-1 are all 12-/12-/10-ring zeolites.

Zeolite TNU-9 has a 3-dimensional channel system. All the channels consist of 10-ring pore openings. There are 2 different channel systems along [010]: one channel has a larger pore size (5.6×5.5 Å) and another channel has a smaller pore size (5.1×5.5 Å). The channel along [10-1] has a pore size of 5.4×5.5 Å. Code TUN is assigned to zeolite TNU-9 by the Structure Commission of the International Zeolite Association (IZA). The aforementioned CON-type and TUN-type zeolites are further described hereinbelow.

Reaction Mixtures for Zeolite Synthesis

In accordance with the present invention, CON-type and TUN-type zeolites may be synthesized by: (a) preparing a reaction mixture containing (1) at least one active source of an oxide selected from the group consisting of oxides of silicon, germanium, and a mixture thereof; (2) one or more active source(s) of an oxide selected from the group consisting of oxides of aluminum, boron, iron, gallium, and mixtures thereof; (3) at least one active source of an element selected from Groups IA and IIA of the Periodic Table; (4) hydroxide ions; (5) water, and (6) a SDA (structure directing agent) selected from the group consisting of SDA dications represented by 1,4-bis(N-cyclohexylpyrrolidinium)butane, 1,5-bis(N-cyclohexylpyrrolidinium)pentane, 1,4-bis(N-cyclohexylpiperidinium)butane, 1,5-bis(N,N-dimethylcyclohexylammonium)pentane, and 1,4-bis(N-cyclopentylpiperidinium)butane; and (b) maintaining the reaction mixture under conditions sufficient to form crystals of the zeolite. Where the zeolite formed in step (b) is an intermediate zeolite, a target zeolite may be prepared therefrom by post-synthesis techniques such as heteroatom lattice substitution techniques and acid leaching.

The composition of suitable reaction mixtures from which the zeolites may be formed are provided in the Examples herein below. Reaction mixtures for the synthesis of SSZ-26 and SSZ-33 are also disclosed in commonly assigned, co-pending U.S. patent application Ser. No. 12/249,770, entitled Method for Preparing SSZ-26/33 Zeolites Using Novel Structure Directing Agents, filed Oct. 10, 2008, the disclosure of which is incorporated by reference herein in its entirety (see, U.S. Publication No. 2009/0060835 (Burton, Jr.)).

Aluminosilicate zeolite SSZ-26 and methods for making it are also described in U.S. Pat. No. 4,910,006 to Zones et al., the disclosure of which is incorporated by reference herein in its entirety. SSZ-26 has a mole ratio of an oxide selected from silicon oxide, germanium oxide and mixtures thereof to an oxide selected from aluminum oxide, gallium oxide, iron oxide and mixtures thereof in the range of 10:1 to 200:1.

Zeolite SSZ-33 and methods for making it are described in U.S. Pat. Nos. 5,120,425 and 4,963,337 to Zones et al., and in U.S. Pat. No. 5,972,204 to Corma et al., as well as in U.S. Publication No. 2009/0060835 A1, the disclosures of each of which is incorporated by reference herein in its entirety. SSZ-33 has a molar ratio greater than about 20:1 of an oxide selected from silicon oxide, germanium oxide and mixtures thereof to an oxide selected from boron oxide or mixtures of boron oxide with aluminum oxide, gallium oxide and iron oxide.

SSZ-26 and SSZ-33 are zeolites which contain a three-dimensional pore system composed of intersecting 10- and 12-ring pores. (See, Lobo et al., "SSZ-26 and SSZ-33: Two Molecular Sieves with Intersecting 10- and 12-Ring Pores" *Science*, Vol. 262. no. 5139, pp. 1543-1546, Dec. 3, 1993). These two zeolites can be characterized as members of a family of materials in which the two end members are formed by the stacking of layers in an ABAB sequence or an ABCABC sequence. The framework formed by the ABAB stacking sequence ("polymorph A") is of orthorhombic symmetry and the framework formed by the ABCABC stacking sequence ("polymorph B") is of monoclinic symmetry. In between these end-member polymorphs there is a whole family of materials that can be characterized by a fault probability "p" of 0%<p>100% (referred to herein as "SSZ-26/33 family"). If the fault probability is p=0%, the end member polymorph B is obtained, and if p=100%, the end member polymorph A is obtained. The aluminosilicate SSZ-26 and the borosilicate SSZ-33 are members of this disorder family of materials and CIT-1 corresponds to a pure or nearly pure polymorph B. (See, CON Framework Datasheet, Baerlocher et al., *Atlas of Zeolite Framework Types*, 6th Ed. (2007)) (See also, CON powder pattern and SSZ33/SSZ26 family, polymorph A-polymorph B powder pattern simulations of disordered intergrowths, Treacy et al., *Collection of Simulated XRD Powder Patterns for Zeolites*, 4th Ed., (2001)).

Zeolite CIT-1 is described, for example, in U.S. Pat. No. 5,512,267 issued Apr. 30, 1996 to Davis et al., the disclosure of which is incorporated by reference herein in its entirety. CIT-1 has a molar ratio greater than about 20:1 of an oxide selected from silicon, germanium oxide and mixtures thereof to an oxide selected from boron oxide or mixtures of boron oxide with aluminum oxide, gallium oxide, iron oxide, titanium oxide and vanadium oxide.

Details of the structure and properties of zeolite TNU-9 are described by Gramm et al. in the journal *Nature*, Vol. 444 (2006) pp. 79-81, by Hong et al. in *J. American Chemical Society*, Vol. 126 (2004) pp. 5817-5826, by Hong et al. in *J. American Chemical Society*, Vol. 129 (2007) pp. 10870-10885, and typical X-ray diffraction patterns of zeolite TNU-9 are disclosed in Korean Patent Application No. 20030082022, the disclosure of each of which is incorporated by reference herein in its entirety.

Structure Directing Agents for Zeolite Syntheses

The 1,4-bis(N-cyclohexylpyrrolidinium)butane and 1,5-bis(N-cyclohexylpyrrolidinium)pentane dication SDAs of the present invention (represented by structures (1) and (2) herein) can be synthesized by reacting a dihaloalkane (such as 1,4-dibromobutane and 1,5-dibromopentane) with N-cyclohexylpyrrolidine. In one embodiment, N-cyclohexylpyrrolidine is synthesized by hydrogenation of 1-pyrrolidino-1-cyclohexene (see, Example 2, hereinbelow). Methods for the hydrogenation of 1-pyrrolidino-1-cyclohexene are taught in Example 7 of U.S. Pat. No. 6,544,495 to Saleh Elomari, issued Apr. 8, 2003.

The 1,5-bis(N,N-dimethylcyclohexylammonium)pentane dication SDA of the present invention (represented by structure (3) herein) can be synthesized by reacting a dihaloalkane (such as 1,5-dibromopentane) with dimethylcyclohexylamine.

The 1,4-bis(N-cyclohexylpiperidinium)butane dication SDA of the present invention (represented by structure (4) herein) can be synthesized by reacting a dihaloalkane (such as 1,4-dibromobutane) with N-cyclohexylpiperidine.

The 1,4-bis(N-cyclopentylpiperidinium)butane dication SDA of the present invention (represented by structure (5) herein) can be synthesized by reacting a dihaloalkane (such as 1,4-dibromobutane) with N-cyclopentylpiperidine. In one embodiment, N-cyclopentylpiperidine is synthesized by hydrogenation of 1-piperidino-1-cyclopentene.

(1)
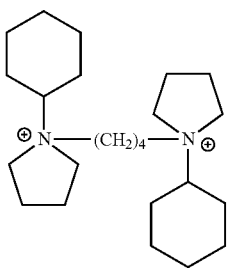
1,4-bis(N-cyclohexylpyrrolidinium)butane dication (2)
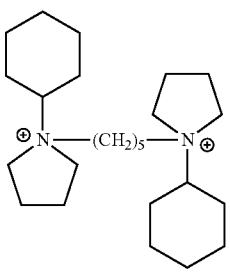
1,5-bis(N-cyclohexylpyrrolidinium)pentane dication (3)
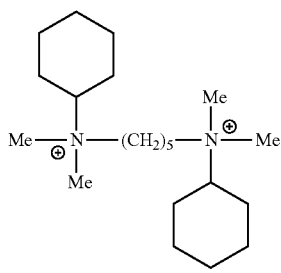
1,5-bis(N,N-dimethylcyclohexylammonium)pentane dication (4)
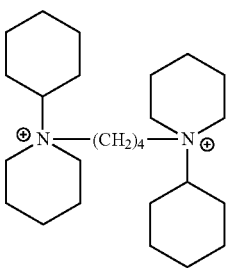
1,4-bis(N-cyclohexylpiperidinium)butane dication (5)
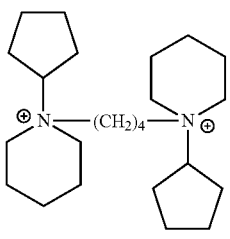
1,4-bis(N-cyclopentylpiperidinium)butane dication Crystallization & Post-Synthesis Treatment of Zeolites Zeolites useful in practicing the instant invention may be prepared by preparing a reaction mixture as described hereinabove; and thereafter maintaining the reaction mixture under crystallization conditions sufficient to form crystals of the zeolite. The reaction mixture may be maintained at an elevated temperature until the crystals of the zeolite are formed. Hydrothermal crystallization is usually conducted under pressure, and usually in an autoclave so that the reaction mixture is subject to autogenous pressure, at a temperature between about 125° C. and 200° C.

The reaction mixture may be subjected to mild stirring or agitation during the crystallization step. It will be understood by a person skilled in the art that the zeolites described herein may contain impurities, such as amorphous materials, unit cells having framework topologies which do not coincide with the zeolite, and/or other impurities.

During the hydrothermal crystallization step, the zeolite crystals can be allowed to nucleate spontaneously from the reaction mixture. The use of crystals of the zeolite as seed material can be advantageous in decreasing the time necessary for complete crystallization to occur. In addition, seeding can lead to an increased purity of the product obtained by promoting the nucleation and/or formation of the zeolite over any undesired phases. When used as seeds, seed crystals may be added in an amount usually between about 1% and 10% of the weight of the source for an oxide of silicon, germanium, or a mixture thereof.

Once the zeolite crystals have formed, the solid product may be separated from the reaction mixture by standard mechanical separation techniques such as filtration. The crystals are water-washed and then dried to obtain the as-synthesized zeolite crystals. The drying step can be performed at atmospheric pressure or under vacuum.

The zeolite can be used as-synthesized, but typically will be thermally treated (calcined). The term "as-synthesized" refers to the zeolite in its form after crystallization, prior to removal of the SDA cation and/or element M, wherein M is an element of Group IA or IIA of The Periodic Table. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the zeolite. The SDA can also be removed by photolysis techniques (e.g. exposing the SDA-containing zeolite product to light or electromagnetic radiation that has a wavelength shorter than visible light under conditions sufficient to selectively remove the organic compound from the zeolite) as described in U.S. Pat. No. 6,960,327 to Navrotsky and Parikh, issued Nov. 1, 2005.

The zeolite can subsequently be calcined in steam, air or inert gas at temperatures ranging from about 200° C. to about 800° C. for periods of time ranging from 1 to 48 hours, or more. Usually, it is desirable to remove the alkali metal cation (if any) by ion exchange and replace it with hydrogen, ammonium, or any desired metal-ion. Where the zeolite formed is an intermediate zeolite, the target zeolite can be achieved using post-synthesis techniques such as heteroatom lattice substitution techniques and acid leaching techniques.

In an embodiment, the zeolites useful in practicing the present invention may be prepared initially in the borosilicate (B—) form and subsequently undergo conversion to the aluminosilicate (Al—) form. In the case of zeolites prepared in the borosilicate form, they can be post-synthetically converted into the aluminosilicate form for use in isomerization processes of the present invention. Procedures for such borosilicate to aluminosilicate conversion are known to those skilled in the art. For example, the post-synthetic conversion of borosilicate zeolites to their aluminosilicate counterparts by treatment with aqueous $Al(NO_3)_3$ solution under acidic conditions is disclosed in U.S. Pat. No. 6,468,501 to Chen et al., the disclosure of which is incorporated by reference herein in its entirety.

Hydroisomerization Catalysts

Zeolites prepared for use in processes of the present invention can be formed into a wide variety of physical shapes. Generally speaking, the molecular sieve can be in the form of a powder, a granule, or a molded product, such as an extrudate, having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or, dried or partially dried and then extruded.

The zeolites of the present invention can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa.

The CON- or TUN-type zeolite hydroisomerization catalysts of the present invention can be used with or without a binder or matrix. Non-limiting examples of inorganic matrix materials include a silica-, alumina- or silica/alumina-based binder. Other matrices such as magnesia, titania, vanadia, chromia, zirconia, and mixtures thereof may also be used.

Catalysts useful for hydroisomerization processes of the present invention are generally bifunctional catalysts that include a hydrogenation/dehydrogenation component and an acidic component. In the present invention, the hydroisomerization catalyst can comprise a Group VIII metal on a CON-type or TUN-type zeolite, typically in the aluminosilicate form. The Group VIII metal compound may be present in an amount to provide sufficient activity for the catalyst to have commercial use. By Group VIII metal compound, as used herein, is meant the metal itself or a compound thereof. Non-limiting examples of Group VIII metals include platinum, palladium, and combinations thereof.

The aforementioned Group VIII metals can be combined with or incorporated into the CON- or TUN-type zeolites by any one of numerous procedures, for example, by co-milling, impregnation, or ion exchange. Processes which are suitable for these purposes are known to those skilled in the art. The Group VIII metal may be present in a CON- or TUN-type zeolite in an amount suitable for catalysis of light paraffins. Metal loaded zeolite catalyst of the present invention may be sufficiently active and selective under hydroisomerization conditions so as to provide a substantial increase in high octane di-branched light paraffins during a single pass through a hydroisomerization zone or reactor. Generally, an amount of metal component combined with the zeolite may typically be in the range from about 0.05 wt. % to about 5.0 wt. %, usually from about 0.1 wt. % and about 3.0 wt. %, and often from about 0.1 wt. % to about 1.0 wt. %, wherein the given wt. % is based on the weight of the zeolite.

Other metals, such as transition metals of Group VIIB (e.g., rhenium) and Group IIIA-VA metals such as gallium, indium, germanium, tin and/or lead may also be combined with the zeolites, in addition to or instead of the aforementioned Group VIII metal. Such metals may be combined with the zeolites of the invention in amounts generally within the same range as given hereinabove with respect to Group VIII metals.

Feedstock

The feedstock or feed stream for hydroisomerization processes of the present invention may comprise primarily normal and singly branched $C_4$ to $C_7$ paraffins, i.e., generally having a relatively low RON. Typically, the feedstock may comprise at least about 10 wt. % normal light paraffins. Optionally, the feed contains benzene which is hydrogenated to cyclohexane in the hydroisomerization process to reduce the benzene content in the gasoline product. Typically, the RON of the feed stream is less than 80, generally not more than about 75, usually not more than about 65, and often not more than about 55. Optionally, the feed is hydrotreated in a hydrotreating process to remove any excess sulfur and/or nitrogen content, prior to the hydroisomerization process.

Hydroisomerization Product

The product of the hydroisomerization process of the present invention comprises more highly branched $C_4$-$C_7$ paraffins, and primarily branched $C_5$-$C_6$ isomers. Typically, the RON of the product is more than about 80, generally at least about 85, usually at least about 90, and often at least about 95. In some embodiments, the product may contain a certain amount of cyclohexane, which may be produced via hydrogenation of benzene during the hydroisomerization process, thereby leading to a reduction in the benzene content of the gasoline product.

According to one aspect of the present invention, the selectivity of CON- and TUN-type zeolite catalysts results in the preferential production of the highest octane $C_6$ isomer, namely 2,3-dimethylbetane (RON 101.0), as shown by the 2,3-dimethylbutane:2,2-dimethylbutane mole ratio (>1.0) of the product (see, e.g., Example 8). Generally, the product stream of processes of the present invention have a 2,3-dimethylbutane:2,2-dimethylbutane mole ratio of at least about 1, typically greater than about 1.0, and in some embodiments at least about 5.

While not being bound by theory, a possible mechanism to explain the selective production of the higher octane 2,3-dimethylbutane isomer over the lower octane 2,2-dimethylbutane in the hydroisomerization reaction of $C_6$ paraffins catalyzed by the CON- and TUN-type zeolite catalysts of the present invention is as follows. Both 12- and 10-ring pores of the CON-type zeolites will admit all the isomers of $C_6$ paraffins (n-hexane, 2-methylpentane, 3-methylpentane, 2,2-dimethylbutane and 2,3-dimethylbutane) to be adsorbed and produced inside the channel systems of these zeolites. However, the size of the 10-ring pores of these zeolites becomes especially critical to the diffusion of the 2,2-dimethylbutane molecules (the bulkiest among all of the $C_6$ paraffin isomers). In other words, the 2,2-dimethylbutane molecules produced inside the channel systems of these zeolites cannot diffuse out of the 10-ring channels as easily as the molecules of 2,3-dimethylbutane and other $C_6$ isomers. In the confined space of the 10-ring channels of the CON-type zeolites, 2,2-dimethylbutane may not be readily formed and/or may be reversibly converted to other less bulky $C_6$ isomers. As a result, the highest octane $C_6$ isomer 2,3-dimethylbutane (RON 101.0) is produced over 2,2-dimethylbutane (RON 91.8) in the CON-type zeolites. It is believed that the sizes of the 12-ring pores of the CON-type zeolites are large enough that they do not have any distinguishable influence on the selectivity between 2,3-dimethylbutane and 2,2-dimethylbutane. As demonstrated by other 12-ring zeolites, such as zeolite Y, the selectivity between 2,3-dimethylbutane and 2,2-dimethylbutane is predominantly controlled by thermodynamics when the isomerization reaction of $C_6$ paraffins occurs in a 12-ring zeolite.

As for the TUN-type zeolites which have only 10-ring channels, it is believed that, like the 10-ring channels of CON-type zeolites, the size of the 10-ring pores of these zeolites becomes especially critical to the diffusion of the 2,2-dimethylbutane molecules (the bulkiest among all of the $C_6$ paraffin isomers). In other words, the 2,2-dimethylbutane molecules produced inside the channel systems of these zeolites cannot diffuse out of the 10-ring channels as easily as the molecules of 2,3-dimethylbutane and other $C_6$ isomers. In the confined space of the 10-ring channels of the TUN-type zeolites, 2,2-dimethylbutane may not be readily formed and/or may be reversibly converted to other less bulky $C_6$ isomers. As a result, the highest octane $C_6$ isomer 2,3-dimethylbutane (RON 101.0) is produced over 2,2-dimethylbutane (RON 91.8) in the TUN-type zeolites.

Process Conditions

During processes of the present invention, the light paraffin feed stream may be contacted with the CON- or TUN-type zeolite based catalyst under hydroisomerization conditions. Typically, the contacting of the light paraffin feed stream with the CON- or TUN-type zeolite based catalyst occurs at a temperature in the range of from about 150° F. to about 700° F., at a pressure ranging from about 50 psig to about 2000 psig, a hydrocarbon feed LHSV ranging from about 0.5 to about 5 $h^{-1}$, and a molar ratio of hydrogen to hydrocarbon ranging from about 0.5 to about 10. Optionally, the catalysts can be pre-sulfided to lower the hydrogenolysis activity. Procedures that are suitable for pre-sulfiding metal-loaded zeolite catalysts are known to those skilled in the art.

In some embodiments, where the conversion of the hydrocarbon feedstock is lower than targeted, or the yield of the preferred product, e.g., 2,3-dimethylbutane, is lower than targeted, a process of the present invention may optionally include a separation stage for recovering at least a portion of the unconverted feedstock. Optionally, at least a portion of the feed stream including any unconverted feedstock may be recycled to the hydroisomerization unit or zone.

Catalysts based on the CON- and TUN-type zeolites described herein have high levels of activity for the hydroisomerization of light paraffins. In hydroisomerization processes of the present invention, CON- and TNU-type zeolite catalysts also show high selectivity in the conversion of n-hexane to the high octane $C_6$ isomer 2,3-dimethylbutane (RON 101) over the lower octane $C_6$ isomer 2,2-dimethylbutane (RON 91.8), in comparison with prior art hydroisomerization processes. Zeolite catalysts useful in processes of the present invention can be readily regenerated following catalyst deactivation.

In situations where the catalyst may be deactivated by coke deposit or other poisons, the catalyst activity can be rejuvenated via catalyst regeneration. Procedures suitable for the regeneration of zeolite catalysts are known in the art. In addition, zeolite catalysts of the present invention are environmentally benign since they are not chlorinated to boost their acidity.

According to one aspect of the present invention, a process for isomerizing light paraffins may comprise contacting a hydrocarbonaceous feed stream with a zeolite catalyst in a hydroisomerization zone under hydroisomerization conditions in the presence of hydrogen. Typically, the feedstock may comprise a refinery stream comprising predominantly $C_4$ to $C_6$ paraffins. Generally, the feed stream may comprise at least about 10 wt. % normal $C_4$ to $C_6$ paraffins. In an embodiment, the feed stream may comprise primarily n-pentane and n-hexane.

The hydroisomerization conditions for processes of the present invention may include a temperature generally in the range from about 150° F. to about 700° F., typically from about 400° F. to about 650° F., and often from about 450° F. to about 600° F. In an embodiment, the hydroisomerization conditions may include a temperature at or about the temperature for maximum isomer yield of one or more light normal paraffins. The temperature for maximum isomer yield from a particular feed stream (e.g., comprising one or more light normal paraffins) may be determined empirically for a given zeolite catalyst, e.g., by performing hydroisomerization of the feed stream over a range of temperatures under defined conditions, and analyzing the composition of the product stream for each hydroisomerization temperature. The product analysis may be conducted, for example, by on-line GC analysis. Hydroisomerization temperatures may be successively increased, e.g., in 5° F.-10° F. increments from a starting hydroisomerization temperature (e.g., about 400° F.), until isomer yields in the product stream from the reactor have peaked. Naturally, the temperature for maximum isomer yield may vary depending on the composition and activity of the zeolite catalyst, and on other factors.

The hydroisomerization conditions for processes of the present invention may further include a pressure typically in the range from about 50 to about 2000 psig, usually from about 100 to about 1000 psig, and often from about 150 to about 400 psig; an LHSV typically in the range from about 0.5 to about 5, usually from about 0.5 to about 3, and often from about 0.75 to about 2.5; and a hydrogen/hydrocarbon ($H_2$/HC) mole ratio typically in the range from about 0.5 to about 10, usually from about 1 to about 10, and often from about 2 to about 8.

The hydroisomerization of light normal paraffins according to the present invention may be performed in a hydroisomerization zone or reactor. Various reactor types may be useful for practicing the present invention. For example, a hydrocarbonaceous feed (e.g., containing substantial amounts of light paraffins) can be contacted with the zeolite catalyst in a fixed bed system, a moving bed system, a fluidized system, a batch system, or combinations thereof. In a fixed bed system, the preheated feed is passed into at least one reactor that contains a fixed bed of the catalyst prepared from material comprising the zeolite catalyst of the invention. The flow of the feed can be upward, downward or radial. The reactors can be equipped with instrumentation to monitor and control temperatures, pressures, and flow rates. Multiple beds may also be used in conjunction with processes of the invention, wherein two or more beds may each contain a different catalytic composition, at least one of which may comprise a CON- or TUN-type zeolite of the present invention.

A range of hydroisomerization conditions for practicing the present invention were described hereinabove. Exemplary hydroisomerization conditions may include a temperature in the range from about 400 to about 650° F., a pressure in the range from about 150 to about 450 psig, an LHSV in the range from about 0.5 to 3, and a $H_2$/HC molar ratio in the range from about 2 to about 8.

A zeolite catalyst suitable for use in processes according to the instant invention may comprise a CON-type zeolite, a TUN-type zeolite, or a combination thereof. CON-type zeolites useful in practicing the present invention may include SSZ-26, SSZ-33, and CIT-1. A TUN-type zeolite useful in practicing the present invention is exemplified by zeolite TNU-9. Typically, each of these zeolites may be used in the aluminosilicate form.

In an embodiment, a zeolite catalyst for conducting hydroisomerization processes of the present invention may comprise aluminosilicate SSZ-26. The SSZ-26 may be prepared generally as described hereinabove, e.g., by contacting under crystallization conditions: (1) at least one source of silicon oxide; (2) at least one source of aluminum oxide; (3) at least one source of an element selected from Group IA or IIA of the Periodic Table; (4) hydroxide ions; and (5) a dication of a structure directing agent (SDA). The SDA for synthesizing aluminosilicate SSZ-26 may comprise, for example 1,4-bis(N-cyclohexylpyrrolidinium)butane, 1,5-bis(N-cyclohexylpyrrolidinium)pentane, or 1,4-bis(N-cyclohexylpiperidinium)butane.

In another embodiment, a zeolite catalyst for hydroisomerization processes of the present invention may comprise aluminosilicate SSZ-33. In a subembodiment, the SSZ-33 may be synthesized initially as borosilicate SSZ-33, and thereafter the B-SSZ-33 may be converted to Al-SSZ-33 by replacing boron in the framework of the borosilicate SSZ-33 with aluminum. The borosilicate SSZ-33 may be prepared generally as described hereinabove, e.g., by contacting under crystallization conditions: (1) at least one source of silicon oxide; (2) at least one source of boron oxide; (3) at least one source of an element selected from Group IA or IIA of the Periodic Table; (4) hydroxide ions; and (5) a dication of a structure directing agent (SDA). The SDA for synthesizing borosilicate SSZ-33 may comprise, for example 1,5-bis(N,N-dimethylcyclohexylammonium)pentane, 1,4-bis(N-cyclohexylpiperidinium)butane, or 1,4-bis(N-cyclopentylpiperidinium)butane.

In a further embodiment, a zeolite catalyst for conducting hydroisomerization processes of the present invention may comprise aluminosilicate TNU-9. The TNU-9 may be prepared generally as described hereinabove, e.g., by contacting under crystallization conditions: (1) at least one source of silicon oxide; (2) at least one source of aluminum oxide; (3) at least one source of an element selected from Group IA or HA of the Periodic Table; (4) hydroxide ions; and (5) a dication of a structure directing agent (SDA). The SDA for synthesizing aluminosilicate TNU-9 may comprise, for example, 1,4-bis(N-methylpyrrolidinium)butane.

In an embodiment, a zeolite catalyst for conducting hydroisomerization processes of the present invention may comprise a Group VIII metal. The Group VIII metal may typically be present in an amount ranging from about 0.05 wt % to about 5 wt % of Group VIII metal based on the weight of the zeolite, usually in the range from about 0.1 wt % to about 3 wt %, and often from about 0.1 wt % to about 1 wt %. Exemplary Group VIII metals include Pt, Pd, and mixtures thereof.

In an embodiment of an isomerization process of the present invention, a hydrocarbonaceous feed stream comprising light paraffins may be contacted with a zeolite catalyst in a hydroisomerization zone under hydroisomerization conditions in the presence of hydrogen to provide a product stream enriched in high octane paraffin isomers. The hydrogen may be provided in an amount sufficient to provide a hydrogen/hydrocarbon ($H_2$/HC) molar ratio typically in the range from about 0.5 to about 10, usually from about 1 to about 10, and often from about 2 to about 8. In an embodiment, the hydrocarbon feed stream may be comprised predominantly of $C_4$-$C_6$ paraffins, and in a subembodiment the feed stream may comprise predominantly $C_5$-$C_6$ n-paraffins. In a further subembodiment, the feed stream may generally comprise at least about 10 vol % n-hexane, typically at least about 20 vol % n-hexane, and often at least about 50 vol % n-hexane.

A product stream resulting from hydroisomerization processes of the present invention may comprise dimethylbutane, which term may be used herein to refer generically and/or collectively to the two $C_6$ isomers 2,2-dimethylbutane and 2,3-dimethylbutane. Of these, the latter has the higher RON (Table 1) and is accordingly the most desirable isomer in the product stream of processes of the present invention. In an embodiment, the product stream may generally comprise at least about 15 mol % of dimethylbutane, and typically the product stream may comprise at least about 20 mol % of dimethylbutane. In a subembodiment, the product stream may generally comprise at least about 10 mol % of 2,3-dimethylbutane, and typically the product stream may comprise at least about 12 mol % of 2,3-dimethylbutane.

In an embodiment, the product stream resulting from hydroisomerization processes of the present invention may comprise 2,2-dimethylbutane and 2,3-dimethylbutane, wherein a 2,3-dimethylbutane/2,2-dimethylbutane mole ratio of the product stream is at least about 1. In a subembodiment, the product stream resulting from hydroisomerization processes of the present invention may have a 2,3-dimethylbutane/2,2-dimethylbutane mole ratio of at least about 5. The product stream may further comprise 2-methylpentane and 3-methylpentane.

In a subembodiment, the feed stream may be contacted with a zeolite catalyst of the present invention during a single pass of the feed stream through the hydroisomerization zone or reactor to provide a product stream comprising at least about 15 mol % of dimethylbutane.

According to another embodiment of the present invention, a process for isomerizing light paraffins may comprise contacting a feed stream comprising at least about 10 vol % n-hexane with a zeolite catalyst in a hydroisomerization zone under hydroisomerization conditions in the presence of hydrogen, wherein the n-hexane is selectively isomerized to 2,3-dimethylbutane to provide a product stream having a 2,3-dimethylbutane/2,2-dimethylbutane mole ratio greater than about 1. As non-limiting examples, zeolite catalysts comprising Al-SSZ-26 and Al-TNU-9 provide $C_6$ isomers having a 2,3-dimethylbutane/2,2-dimethylbutane mole ratio of 1.29 and 5.04, respectively, at maximum isomer yield (see, e.g., Example 8 and Table 2).

In an embodiment of an isomerization process of the present invention, the feed stream may generally have a Research Octane Number (RON) of not more than about 75, typically not more than about 65, and in some embodiments not more than about 55; in contrast, the product stream may have an RON of generally at least about 85, typically at least about 90, and in some embodiments at least about 95.

The following examples demonstrate but do not limit the present invention.

EXAMPLES

Example 1

Synthesis of
1,4-bis(N-cyclohexylpiperidinium)butane Dication

In a Teflon liner for a 125 mL Steel Parr autoclave, 10.6 g N-cyclohexylpiperidine (Lancaster) was added to 50 mL acetonitrile. Then 6.19 g 1,4-dibromobutane was added to the mixture. The liner was then capped and sealed inside the autoclave. The sealed autoclave was then placed inside an oven and heated under static conditions at 75° C. for 5 days. The autoclave was then removed from the oven and allowed to cool to room temperature. The solid product from the reaction was then removed by filtration and washed with acetonitrile to remove undissolved HBr salts of N-cyclohexylpiperidine. The solids were then washed with acetone and ethyl ether and they were then allowed to dry to give about 8.75 g of the diquaternary product. After drying, the purity of the product salt was verified by $^1$H and $^{13}$C NMR. The purified crop was ion-exchanged into the hydroxide form by dissolving the salts in water and adding a two-fold excess of AG-1-X8 hydroxide anion-exchange resin (Bio-Rad Laboratories, Inc.) and allowing the exchange to occur overnight. The resin was then removed by filtration and the resultant SDA solution was titrated to determine the hydroxide concentration.

Example 2

Synthesis of
1,4-bis(N-cyclohexylpyrrolidinium)butane Dication
from N-cyclohexylpyrrolidine N-Cyclohexylpyrrolidine was synthesized by hydrogenation of 1-pyrrolidino-1-cyclohexene (Sigma-Aldrich) per the teachings in Example 7 of U.S. Pat. No. 6,544,495 to Saleh Elomari. 1,4-bis(N-cyclohexylpyrrolidinium)butane dication was then synthesized from N-cyclohexylpyrrolidine as follows. In a 250 mL round-bottom flask, 18.84 g N-cyclohexylpyrrolidine was dissolved in 75 mL acetone. Then 11.96 g 1,4-dibromobutane was added to the solution. The resultant solution was allowed to sit at room temperature for three weeks. The acetone was then removed by rotoevaporation. The resultant residues were then dissolved in isopropanol and the solution was then intermittently refluxed for 2-3 hour periods over the course of a week. After each refluxing period, the isopropanol was removed and the residues were washed with acetone. The product diquaternary ammonium salt then precipitated as a tan solid. The tan solid was then isolated by vacuum filtration. The resultant solid was then thoroughly rinsed with isopropanol to remove any reactant or monoquaternary products. The product was subsequently rinsed with acetone and then with ethyl ether.

After drying, the purity of the product salt was verified by $^1$H and $^{13}$C NMR. The filtrates were then combined and the refluxing of the isopropanol solutions was repeated to obtain additional product. The purified crops were then combined and ion-exchanged into the hydroxide form by dissolving the salts in water and adding a two-fold excess of AG-1-X8 hydroxide anion-exchange resin (Bio-Rad Laboratories, Inc.) and allowing the exchange to occur overnight. The resin was then removed by filtration and the resultant SDA solution was titrated to determine the hydroxide concentration.

Example 3

Synthesis of Borosilicate SSZ-33 Using
1,4-bis(N-cyclohexylpiperidinium)butane Dication 3.52 g of a hydroxide solution of 1,4-bis(N-cyclohexylpiperidinium)butane ([OH$^-$]=0.51 mmol/g) synthesized per Example 1, 0.72 g 1 N sodium hydroxide, and 4.12 g deionized water were mixed together in a Teflon liner. Then 0.036 g sodium borate decahydrate was dissolved in the solution. Next 0.54 g CAB-O-SIL M-5 fumed silica (Cabot Corporation) was added to the solution and mixed to create a uniform gel. The liner was then capped and placed within a Parr Steel autoclave reactor. The autoclave was then fixed in a rotating spit (43 rpm) within an oven heated at 160° C. for 5 days. The solid products were recovered from the cooled reactor by vacuum filtration and washed with copious quantities of water. The resulting zeolite product was analyzed by powder XRD, which indicated the material was a SSZ-33.

A portion of the as-synthesized B-SSZ-33 product was calcined as follows. The sample was heated in a muffle furnace from room temperature up to 1004° F. at a steadily increasing rate over a seven-hour period. The sample was maintained at 1004° F. for four more hours and then taken up to 1112° F. for an additional four hours. The atmosphere was nitrogen at a rate of 20 standard cubic feet per minute with a small amount of air being bled into the flow. The resulting calcined zeolite product was analyzed by powder XRD, which indicated the material was a SSZ-33.

Example 4

Synthesis of Aluminosilicate SSZ-26 Using
1,4-bis(N-cyclohexylpyrrolidinium)butane Dication 6.87 g of a hydroxide solution of 1,4-bis(N-cyclohexylpyrrolidinium)butane ([OH$^-$]=0.50 mmol/g) synthesized per Example 2, 3.00 g 1 N sodium hydroxide, and 1.09 g deionized water were mixed together in a Teflon liner. Next 0.54 g CAB-O-SIL M-5 fumed silica (Cabot Corporation) and 0.25 g LZY-62 zeolite Y were added to the solution and mixed to create a uniform gel. 0.05 g of seeds from Example 3 were then added to the gel. The liner was then capped and placed within a Parr Steel autoclave reactor. The autoclave was then fixed in a rotating spit (43 rpm) within an oven heated at 160° C. for 7 days. The solid products were recovered from the cooled reactor by vacuum filtration and washed with copious quantities of water. The resulting zeolite product was analyzed by powder XRD and SEM. Powder XRD analysis indicated the sample was SSZ-26.

A portion of the as-synthesized Al-SSZ-26 product was calcined as follows. The sample was heated in a muffle furnace from room temperature up to 1004° F. at a steadily increasing rate over a seven-hour period. The sample was maintained at 1004° F. for four more hours and then taken up to 1112° F. for an additional four hours. The atmosphere was nitrogen at a rate of 20 standard cubic feet per minute with a small amount of air being bled into the flow. The resulting calcined zeolite product was analyzed by powder XRD, which indicated the material was SSZ-26.

Example 5

Post-Synthetic Preparation of Al-SSZ-33

Al-SSZ-33 was prepared from B-SSZ-33 via the method described in U.S. Pat. No. 6,468,501, as follows: 3 grams of the calcined B-SSZ-33 of Example 3 were combined with 300 grams of 1 M aqueous Al(NO$_3$)$_3$ solution and heated in a Teflon-lined autoclave under static conditions at 212° F. for 100 hours. The resulting Al-SSZ-33 product was then washed with 1 liter of water, filtered, and air-dried at room temperature in vacuum filter. The resulting calcined zeolite product was analyzed by powder XRD, which indicated the material was a SSZ-33.

Example 6

Synthesis of Aluminosilicate TNU-9 using
1,4-bis(N-methylpyrrolidinium)butane Dication TNU-9 was synthesized according to Korean Patent Application No. 20030082022. 7.03 g of a hydroxide solution of 1,4-bis(N-methylpyrrolidinium)butane ([OH$^-$]=0.64 mmol/g), 4.26 g deionized water, 0.26 g sodium hydroxide (98%) pellets, and 0.46 g sodium bromide were mixed together in a Teflon liner until the solid components were completely dissolved. Then 0.04 g Reheis F2000 aluminum hydroxide was dissolved in the solution. Next 0.90 g Cabosil M-5 fumed silica was added to the solution and mixed to create a uniform gel. The liner was then capped and sealed within a Parr Steel autoclave reactor. The autoclave was then fixed in a rotating spit (43 rpm) within an oven heated at 320° F. for 14 days. The solid products were subsequently recovered from the cooled reactor by vacuum filtration and washed with copious quantities of water. The recovered solids were then allowed to dry in an oven at 203° F. overnight.

The product from the above synthesis was next calcined by heating the zeolite in a muffle furnace in a nitrogen stream with a slight bleed of air at a rate of about 20 standard cubic feet per minute. The zeolite was heated to 248° F. at 1.8° F./min, allowed to remain at 248° F. for 2 hours, heated to 1103° F. at 1.8° F./min, and allowed to remain at 1103° F. for 5 hours. The zeolite was then allowed to cool to ambient temperature. The powder X-ray diffraction of the zeolite indicated the material was TNU-9.

Example 7

Preparation of Hydroisomerization Catalysts

Al-SSZ-26, Al-SSZ-33 and TNU-9 prepared in Examples 4, 5, and 6, respectively, were separately ion exchanged with aqueous $NH_4NO_3$ solution to create their $NH_4$-forms three times under reflux. They were then separately ion exchanged with aqueous $(NH_3)_4Pd(NO_3)_2$ solution to load each zeolite with 0.5 wt % Pd. The resulting catalysts were subsequently calcined by heating in air at 450° F. for 5 hours. The Pd-loaded zeolites were reduced in hydrogen prior to the catalytic experiments (Example 8).

Example 8 n-Hexane Hydroisomerization Over Al-SSZ-26, Al-SSZ-33 and Al-TNU-9

The catalytic reactions of hydroisomerization of n-hexane were carried out using samples of SSZ-26, SSZ-33, and TNU-9 (Example 7) in a flow type fixed bed reactor with pure n-hexane as feed, at temperatures corresponding to the maximum isomer yield for each zeolite sample. The temperature for maximum isomer yield for each sample of zeolite catalyst was determined by product analysis (on-line GC) over a range of successively increased temperatures (10° F. increments) starting at a temperature of 400° F., until isomer yields in the product stream of each catalyst sample reached a maximum. The temperature for maximum isomer yield for each zeolite catalyst tested is presented in Table 2. The hydroisomerization conditions included a pressure of 200 psig, an LHSV of 1 h$^{-1}$, and a molar $H_2$ to hydrocarbon ratio of 6:1. The reaction products were analyzed with an on-line GC to quantify each of the $C_6$ alkane isomers, and the results are shown in Table 2.

Example 9

Hydroisomerization of n-hexane over Zeolites Y, mordenite, ZSM-5 and SSZ-32

The hydroisomerization of n-hexane was carried out over Pd/Y (3-dimensional, 12-ring zeolite), Pd/mordenite (1-dimensional, 12-ring zeolite), Pd/ZSM-5 (3-dimensional, 10-ring zeolite) and Pd/SSZ-32 (1-dimensional, 10-ring zeolite), in a flow type fixed bed reactor with pure n-hexane as feed at the temperature, pressure, LHSV, and molar $H_2$ to hydrocarbon ratio as described in Example 8. The results at the respective temperatures corresponding to maximum isomer yield are also presented in Table 2.

In the hydroisomerization of n-hexane with a CON- or TUN-type zeolite catalyst the highest octane 2,3-dimethylbutane isomer was preferentially formed with about 80 mol % conversion of the n-hexane with not more than 2 mol % cracking. The results demonstrate that processes of the present invention using the catalysts based on CON-type and TUN-type zeolites advantageously provide selectivity to the highest octane $C_6$ isomer, namely 2,3-dimethylbutane with a RON of 101.0, rather than the lower octane 2,2-dimethylbutane (RON 91.8). In contrast, the latter isomer was preferentially formed in prior art processes.

Although ZSM-5 and SSZ-32 gave high 2,3-dimethylbutane/2,2-dimethylbutane ratios, the total dimethylbutane produced during n-hexane hydroisomerization by these zeolites is very small (3.2 and 2.2 mol %, respectively, at maximum isomer yield), as compared with the total dimethylbutane production by the CON- and TUN-type zeolites (see, Table 2).

TABLE 2

Hydroisomerization of n-Hexane over Various Pd/Zeolites at Maximum Isomer Yield

| Zeolite | Temperature at maximum isomer yield, ° F. | Maximum isomer yield, mol % | Distribution, mol % | | | | |
|---|---|---|---|---|---|---|---|
| | | | 2,2-dimethyl-butane | 2,3-dimethyl-butane | 2-methyl-pentane | 3-methyl-pentane | total |
| SSZ-26 | 500 | 78.8 | 9.9 | 12.8 | 47.0 | 30.3 | 100.0 |
| SSZ-33 | 520 | 79.1 | 11.9 | 12.4 | 46.0 | 29.7 | 100.0 |
| TNU-9 | 500 | 77.4 | 2.6 | 13.1 | 51.8 | 32.5 | 100.0 |
| Y | 580 | 79.5 | 21.9 | 10.0 | 41.1 | 27.0 | 100.0 |
| Mordenite | 560 | 78.6 | 21.5 | 10.8 | 40.7 | 27.0 | 100.0 |
| ZSM-5 | 500 | 74.4 | 0.2 | 3.0 | 59.6 | 37.2 | 100.0 |
| SSZ-32 | 580 | 68.5 | 0.1 | 2.1 | 59.0 | 38.8 | 100.0 |

What is claimed is:

1. A hydroisomerization process, comprising:
   contacting a hydrocarbonaceous feed stream containing $C_4$-$C_6$ paraffins with a catalyst under hydroisomerization conditions in the presence of hydrogen to produce a hydroisomerization product;
   the catalyst comprising an aluminosilicate zeolite selected from the group consisting of CON- and TUN-type aluminosilicate zeolites, and at least one Group VIII metal.

2. The process of claim 1, wherein the catalyst comprises a zeolite selected from the group consisting of CON-type zeolites.

3. The process of claim 1, wherein the catalyst comprises a zeolite selected from the group consisting of TUN-type zeolites.

4. The process of claim 1, wherein the zeolite is selected from the group consisting of SSZ-26, SSZ-33, CIT-1, and TNU-9.

5. The process of claim 1, wherein the feed stream comprises 10 wt. % normal and singly branched $C_4$ to $C_7$ paraffins.

6. The process of claim 5, wherein the product stream comprises 2,2-dimethylbutane and 2,3-dimethylbutane, and wherein the product stream has a 2,3-dimethylbutane/2,2-dimethylbutane mole ratio of the product stream is at least about 1.

7. The process of claim 6, wherein the 2,3-dimethylbutane/2,2-dimethylbutane mole ratio is at least about 5.

8. The process of claim 1, wherein the product stream comprises 2,2-dimethylbutane and 2,3-dimethylbutane, and wherein the product stream has a 2,3-dimethylbutane/2,2-dimethylbutane mole ratio of the product stream is at least about 1.

9. The process of claim 8, wherein the 2,3-dimethylbutane/2,2-dimethylbutane mole ratio is at least about 5.

10. The process of claim 1, wherein the catalyst comprises a Group VIII metal in the range from about 0.05 wt % to about 5 wt % based on the weight of the zeolite.

11. The process of claim 1, wherein the catalyst comprises a Group VIII metal in the range from about 0.1 wt % to about 3 wt % based on the weight of the zeolite.

12. The process of claim 1, wherein the catalyst comprises a Group VIII metal in the range from about 0.1 wt % to about 1 wt % based on the weight of the zeolite.

13. The process of claim 1, wherein the Group VIII metal is selected from the group consisting of platinum, palladium, and combinations thereof.

14. The process of claim 13, wherein the catalyst comprises a Group VIII metal in the range from about 0.05 wt % to about 5 wt % based on the weight of the zeolite.

15. The process of claim 1, wherein the hydroisomerization conditions comprise a temperature in the range of from about 150° to about 700° F., at pressure ranging from about 50 psig to about 2000 psig, a hydrocarbon feed LHSV ranging from about 0.5 $h^{-1}$ to about 5 $h^{-1}$, and a molar ratio of hydrogen to hydrocarbon ranging from about 0.5 to about 10.

16. The process of claim 15, wherein the hydroisomerization conditions comprises a temperature in the range of from about 450° to about 600° F.

17. The process of claim 15, wherein the hydroisomerization conditions comprises a pressure in the range of from about 150 psig to about 400 psig.

18. The process of claim 15, wherein the hydroisomerization conditions comprises a LHSV from 0.75 $h^{-1}$ to about 2.5 $h^{-1}$.

19. The process of claim 15, wherein the hydroisomerization conditions comprises a hydrogen/hydrocarbon mole ratio of from about 2 to about 8.

* * * * *